United States Patent
Gammons et al.

(10) Patent No.: US 6,689,155 B2
(45) Date of Patent: Feb. 10, 2004

(54) UPPER BODY CONVECTIVE HEAT THERAPY DEVICE AND METHOD OF MAKING AND USING SAME

(75) Inventors: Clifford Eugene Gammons, Loudon, TN (US); Joseph Greg Jones, Englewood, TN (US)

(73) Assignee: Adroit Medical Systems, Inc., Loudon, TN (US)

( * ) Notice: Subject to any disclaimer, the term of this patent is extended or adjusted under 35 U.S.C. 154(b) by 0 days.

(21) Appl. No.: 09/916,353

(22) Filed: Jul. 27, 2001

(65) Prior Publication Data

US 2003/0023289 A1 Jan. 30, 2003

(51) Int. Cl.$^7$ .................................................. A61F 7/00
(52) U.S. Cl. .................... 607/109; 607/107; 604/423
(58) Field of Search .................... 607/107, 109, 607/104, 110; 5/421, 423

(56) References Cited

U.S. PATENT DOCUMENTS

| | | | | |
|---|---|---|---|---|
| 5,165,400 A | * | 11/1992 | Berke | 607/104 |
| 5,246,656 A | * | 9/1993 | Stephenson et al. | 264/153 |
| 5,300,101 A | * | 4/1994 | Augustine et al. | 607/107 |
| 5,443,488 A | * | 8/1995 | Namenye et al. | 607/104 |
| 5,674,269 A | * | 10/1997 | Augustine | 607/107 |
| 5,860,292 A | * | 1/1999 | Augustine et al. | 607/107 |
| 5,928,274 A | * | 7/1999 | Augustine | 607/107 |
| 6,102,936 A | * | 8/2000 | Augustine et al. | 607/104 |

* cited by examiner

*Primary Examiner*—Linda C. M. Dvorak
*Assistant Examiner*—Jocelyn Ram
(74) *Attorney, Agent, or Firm*—Pitts & Brittian, P.C.

(57) ABSTRACT

A therapy device for providing heated air to the upper body of a patient and a method of making and using the therapy device have been provided. The therapy device is an inflatable U-shaped tube mounted on a base sheet and having a cover sheet. The patient is placed on the base sheet with the patient's head located between the legs of the tube. The cover sheet is placed over the patient's face. A heated air supply tube is connected to the tube and the heated air inflates the tube and heated air is forced out of the exhaust ports of the tube, thereby providing an environment in which a portion of the patient's body is heated. In one embodiment the exhaust ports are slits cut into the tube sheet material, and the slits are parallel to a tangent line of the tube's sealed edge. The method of fabricating the therapy device includes forming the individual pieces, attaching the tube sheets to form a tube, lancing the tube to form exhaust ports, and attaching the remaining pieces. In another embodiment, the exhaust ports are formed by selectively coating the tube sheets with an air impermeable material except for an area bounded by the exhaust ports.

6 Claims, 6 Drawing Sheets

UPPER BODY CONVECTIVE HEAT THERAPY DEVICE AND METHOD OF MAKING AND USING SAME

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of Invention

This invention relates to the field of heat therapy. More specifically, the present invention relates to a disposable hypothermia article for use with a heat source to supply a source of controlled temperature air to a patient's upper body surface.

2. Description of the Related Art

During and after a surgical procedure, it is well known that the loss of body temperature by the patient can lead to hypothermia. Accordingly, it is well known to apply heat to the patient in order to replace the heat that is lost. While heat loss associated with surgery is discussed herein, it is well known that hypothermia is also caused by other circumstances, such as prolonged exposure to extreme cold. No matter what the cause of hypothermia, it is essential to apply heat to the patient in order to either prevent or overcome hypothermia.

One method for applying heat to a patient is by directing warm air toward the patient. Of specific interest is a generally U-shaped hollow tubular member through which heated air is supplied. Typical of the art are those devices disclosed is U.S. Pat. No. 5,165,400, titled "Convective Hyperthermia Article," issued to Berke on Nov. 24, 1992; and U.S. Pat. No. 5,300,101, titled "Method and Apparatus for Treatment of Pediatric Hypothermia," issued to Augustine, et al., on Apr. 5, 1994.

The '400 device disclosed by Berke is a U-shaped device having two substantially parallel legs positioned adjacent to and extending a substantial length of a patient's body, and the device directs heated air to the body. The '400 device has a crosspiece connecting the two legs. The '101 device disclosed by Augustine is a device similar to that disclosed in the '400 patent, except that it fits an infant or small child and includes positionable covering sheets.

It is an objective of this invention to provide a heat therapy device for a patient who is off-pump. It is a further objective to provide a therapy device for the upper body, specifically the head and upper shoulders.

BRIEF SUMMARY OF THE INVENTION

According to one embodiment of the present invention, an upper body convective heat therapy device is provided. The heat therapy device is a light weight disposable convective hypothermia article that provides warm air to a patient's upper body. It is suitable for use in off-pump situations; that is, when the patient is not on life-support, but requires a source of heat.

In one embodiment, the therapy device is a U-shaped tube that is inflated with a heated air supply. The heated air escapes through slits or an air permeable portion of the tube and is directed towards the patient's head and shoulders. The tube is attached to a flat sheet, upon which the patient lies. Attached to the tube is a flat covering sheet that can be positioned over the patient's upper body without restricting access to the patient. The covering sheet forms a tent over the patient and serves to prevent the heated air from escaping. The covering sheet is fabricated of a clear material that permits viewing the face of the patient.

A method of making the therapy device includes cutting or forming tube sheets, gluing or welding them together, forming exhaust ports in the resulting tube, attaching the tube to a base sheet and a cover sheet. A method for selectively warming a patient's upper body is disclosed and includes arranging a therapy device around the patient's head and shoulders, forcing heated air into the device, exhausting air from the device and directing the air to the patient. A cover sheet is used to prevent the heated air from immediately escaping.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Figure 1:
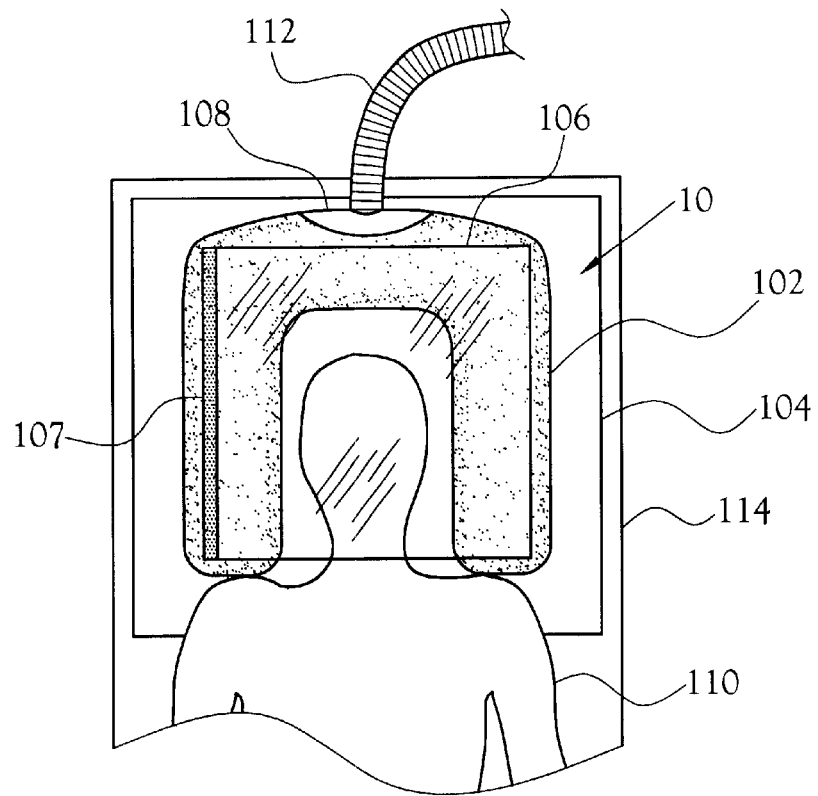
FIG. 1 is a top view of a patient with the therapy device inflated and in place.

An apparatus for an upper body convective heat therapy device 10 and a method of making and using the device 10 is disclosed. Referring to FIG. 1, the therapy device 10 provides warm air to the upper portion of a patient's body 110. A base sheet 104 is placed under the head and shoulders of the patient 110, who is lying on a table or bed 114. The therapy device 10 is connected to a supply hose 112 from a heated air supply (not illustrated). When air is pumped into the therapy device 10, the tube 102 inflates, and heated air is exhausted in a thermal warming zone surrounding a portion of the patient's body 110. A cover sheet 106 prevents the heated air from immediately escaping and is attached 107 to one leg of the tube 102. The cover sheet 106 is positioned over the head of the patient 110 and placed on top of the tube 102.

Figure 2:
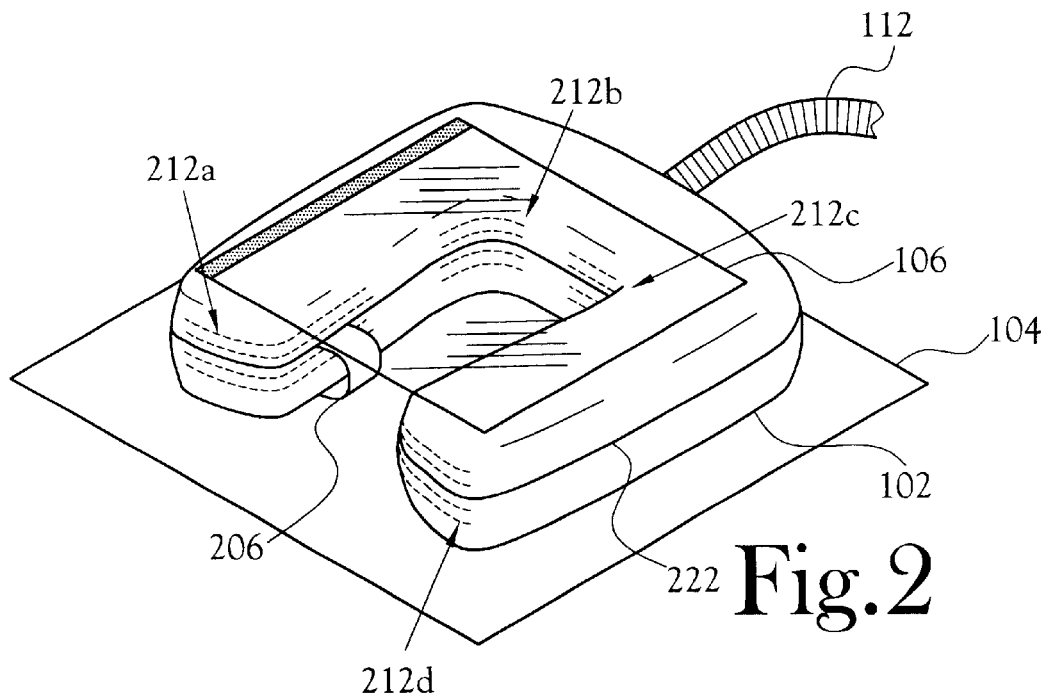
FIG. 2 is a perspective view of the therapy device.

FIG. 2 illustrates a perspective view of an inflated therapy device 10. A first securing strap 206 extending from the seam 222 on the inside of the tube 102 is attached to the base sheet 104. A second securing strap 306 (not illustrated in FIG. 2) extends similarly from the seam opposite that of the first securing strap 206. The securing straps 206, 306 are attached to the base sheet 104 by any of various methods known by those skilled in the art, including welding, double-sided tape, or hot-glue.

The cover sheet 106 is a clear plastic material that forms a tent over the head of the patient 110 and serves to direct the escaping air over a greater portion of the body of the patient 110 by preventing the immediate escape of the heated air. A portion of one end 107 of the cover sheet 106 is attached 107 to one leg of the tube 102 using means known to those skilled in the art, for example, welding, double-sided tape, or hot-glue.

Also shown in FIG. 2 are the exhaust ports or slits 212a, 212b, 212c, 212d through which the heated air forced into the therapy device 10 escapes. The slits 212 are substantially parallel to a line tangent to the nearest seam edge of the tube 102. Alternatively, the slits 212 are substantially perpendicular to the tangent of a circumference of the tube 102 defined by a radius perpendicular to the axis of the tube 102. In another embodiment, the exhaust ports 212 are V-shaped slits; that is, each exhaust port 212 is formed of two slits that are connected at one end and separated at the other end. In still another embodiment, the exhaust ports 212 are holes cut or punched into the tube 102.

In yet another embodiment, the exhaust ports 212 are an integral part of the fabric of the tube 102. That is, the tube 102 is fabricated with material that is air impermeable in all areas except where the exhaust ports 212 are located. For example, the tube 102 is fabricated out of air permeable fabric that is coated with a thin sheet of plastic or other air impermeable material. The coating completely coats the tube 102 material except in the areas in which heated air is to be exhausted. The uncoated areas form the exhaust ports 212 because air escapes from the tube 102 in those areas. Those skilled in the art will recognize that size, number, and location of the exhaust ports 212 can vary depending on the available air flow without departing from the spirit and scope of the present invention.

The exhaust ports 212 cover the surface of the tube 102 in the area in which heated air is desired to be exhausted. In the illustrated embodiment, the tube 102 does not discharge heated air in the area where the patient's ears would be located. The area between exhaust ports 212a and 212b, 212c and 212d is the area of the tube 102 that is adjacent to the ears of the patient 110.

Figure 3:
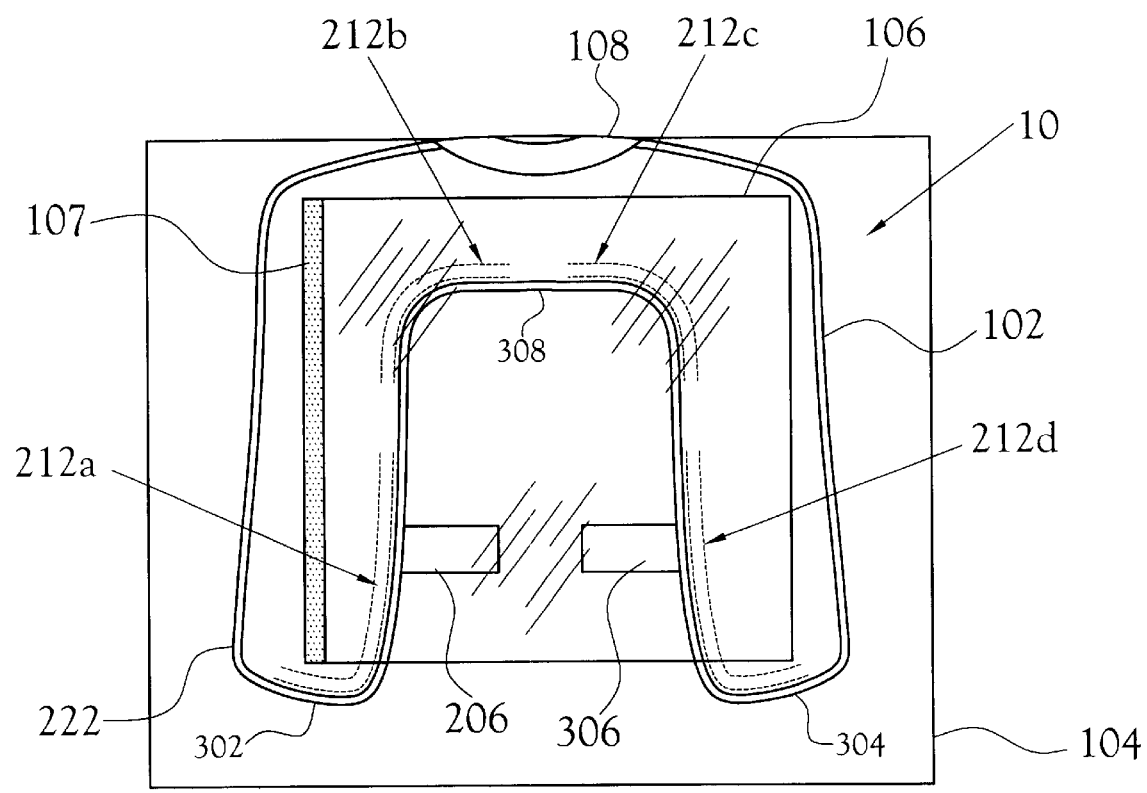
FIG. 3 is a top view of the therapy device.

FIG. 3 shows a therapy device 10 in a deflated state. The legs 302, 304 of the therapy device 10 are splayed out because, when the tube 102 is inflated, the end of the legs 302, 304 draw towards each other. In the illustrated embodiment, the legs 302, 304 are substantially parallel to each other when the therapy device 10 is inflated.

Figure 4:
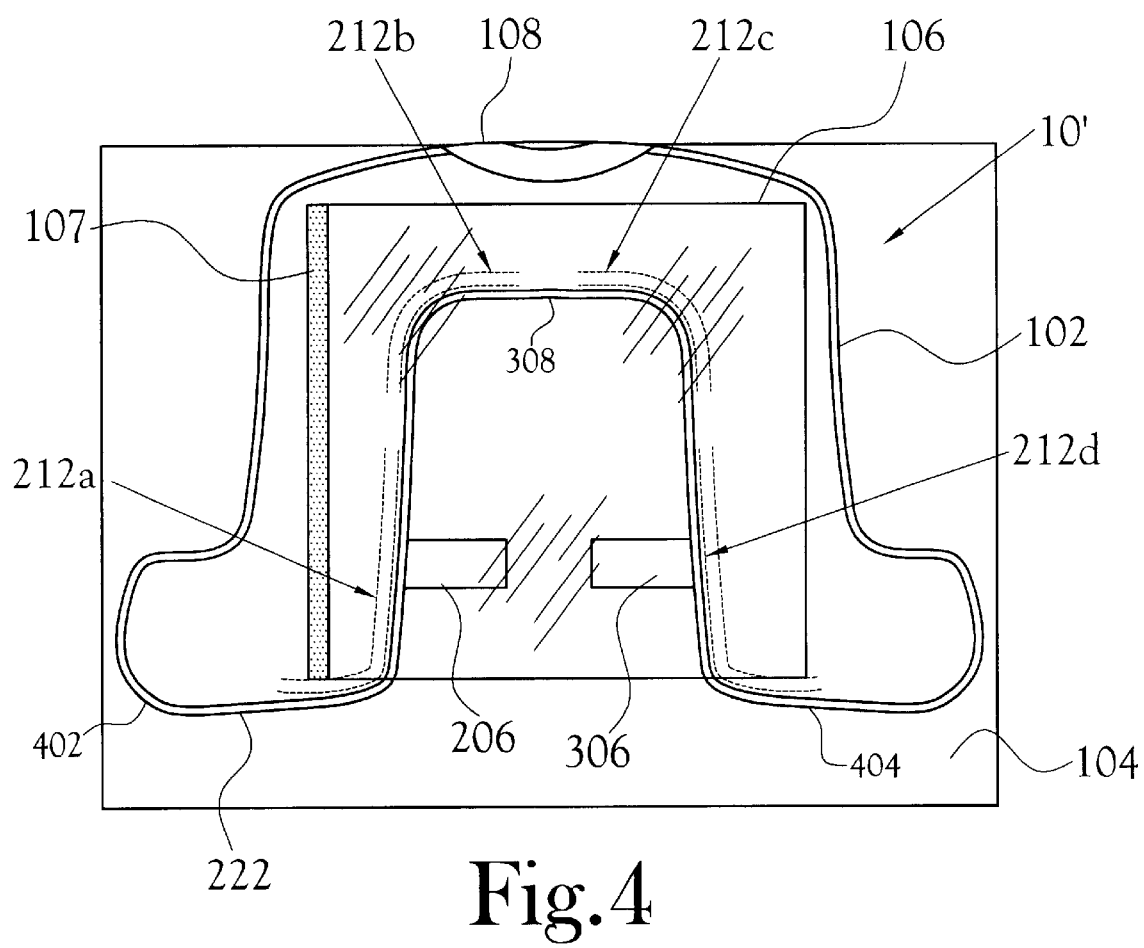
FIG. 4 is a top view of another embodiment of the therapy device.

FIG. 4 shows another embodiment of a therapy device 10' in a deflated state. In this embodiment, the legs 402, 404 of the therapy device 10' have a foot-shaped end portion opposite their connection to the crosspiece 308. The shape of the legs 402, 404 permits the heated air exhausted from the therapy device 10' to be directed across the top of the full width of the shoulders of the patient 110.

Figure 5:
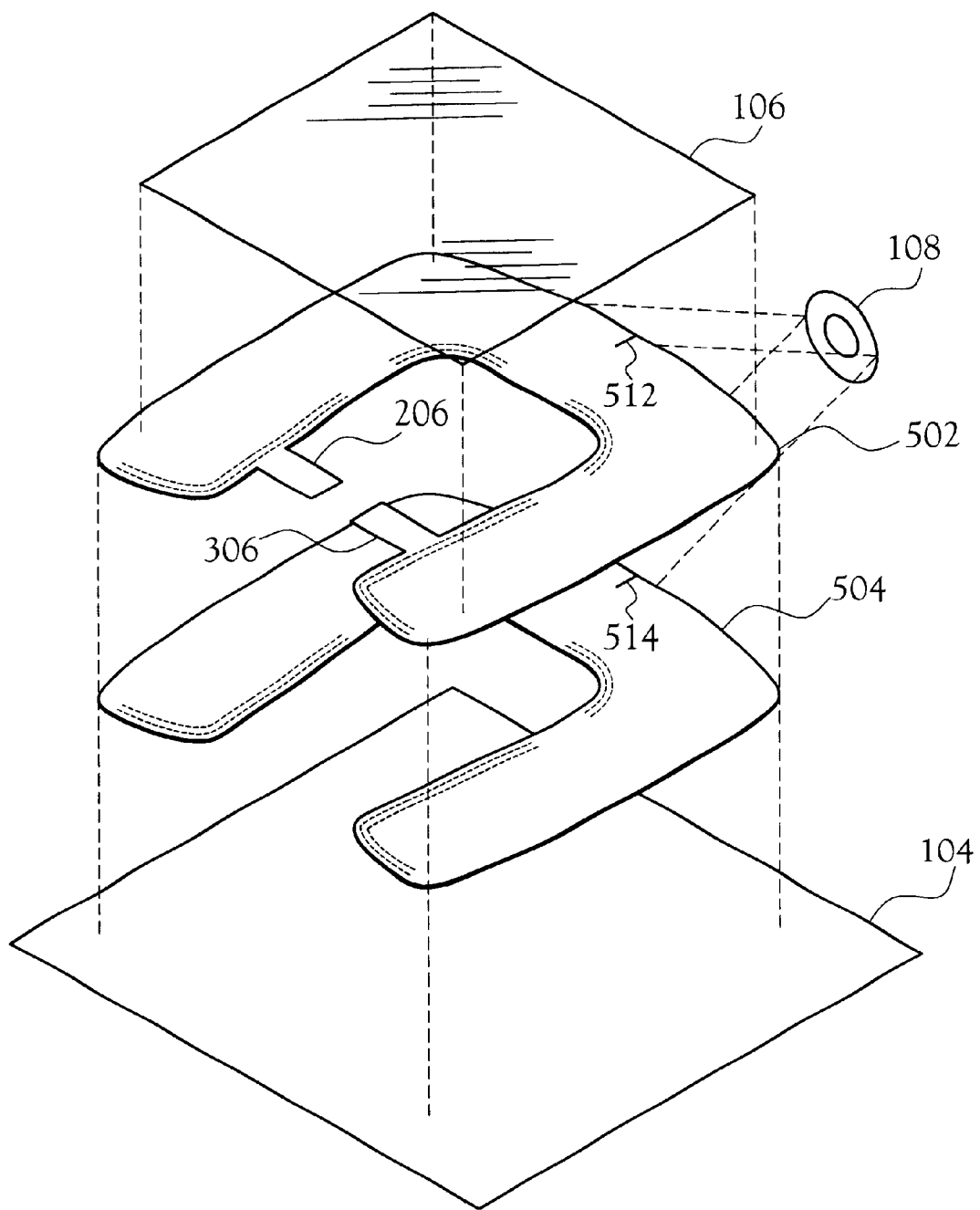
FIG. 5 is an exploded view of the therapy device.

FIG. 5 is an exploded view of the therapy device 10, showing the base sheet 104, two tube sheets 502, 504, the cover sheet 106, and the inlet collar 108. The base sheet 104 is fabricated of the same material as the tube sheets 502, 504, although those skilled in the art will recognize that other material can be used without departing from the spirit and scope of the present invention. The cover sheet 106 is fabricated of a thin-gauge clear plastic that is impermeable to air, for example, 10 gauge clear PVC sheeting.

The tube 102 is made of two tube sheets 502, 504, one on top of the other. The tube sheets 502, 504 are fabricated of a material that is not permeable to air, such as a fabric coated with a plastic. Those skilled in the art will recognize that any of various materials can be used without departing from the spirit and scope of the present invention. Common materials include woven and non-woven fabrics and cellulosics. Material that is air permeable can be coated on at least one side with a thin film of plastic or other air impermeable material. The material is waterproof and impermeable to air.

In the illustrated embodiment, at least one of the tube sheets 502, 504 has two securing straps 206, 306, each extending from a leg 206, 306 towards the other. In another embodiment, the securing straps 206, 306 are separate pieces of material placed between and secured to the tube sheets 502, 504. The two tube sheets 504, 504 are sealed together at their common edges 222. The sheets 502, 504 can be sealed by gluing the opposing surfaces or by welding the plastic coated surfaces. The sealed edge 222 extends into the tube sheet 502, 504 a distance sufficient to provide an air tight seal and provide mechanical strength when the tube 102 is inflated. For fabric with a plastic film, the sealed distance is approximately one-quarter inch.

In the illustrated embodiment, the tube 102 is secured to the base sheet 104 in four places. The tube 102 is attached by securing the seam 222 on both sides of the inlet collar 108 to the base sheet 104. The tube 102 can be glued or welded to the base sheet 104. The tube 102 is secured to the base sheet 104 by the two securing tabs 206, 306 protruding from the tube 102. Each securing tab 206, 306 is folded under its respective tube leg 302, 304 and secured to the base sheet 104.

The inlet collar 108 is secured to the cross-piece of the tube 102. The inlet collar 108 is a section of stiff material, such as paper or cardboard, with a hole in the center sized to accept the nozzle of the heated air supply hose 112. The inlet collar 108 is attached to the tube sheets 502, 504 by gluing it to the fabric. Slits 512, 514 are cut into the tube sheets 502, 504 and provide clearance for the nozzle of the heated air supply hose 112. In the illustrated embodiment, the inlet collar 108 is not secured to the base sheet 104.

Figure 6:
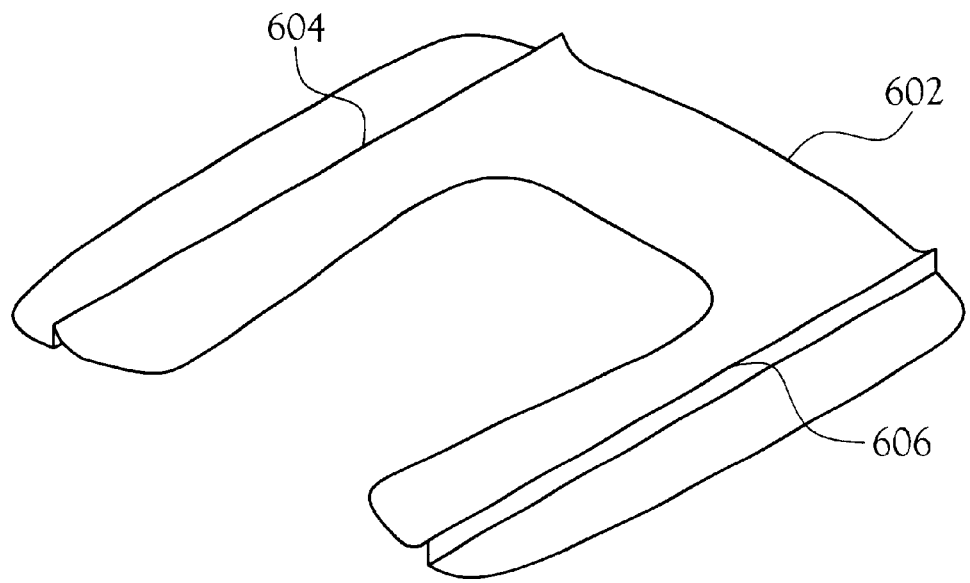
FIG. 6 is a perspective view of one panel of one embodiment the device.
Figure 7:
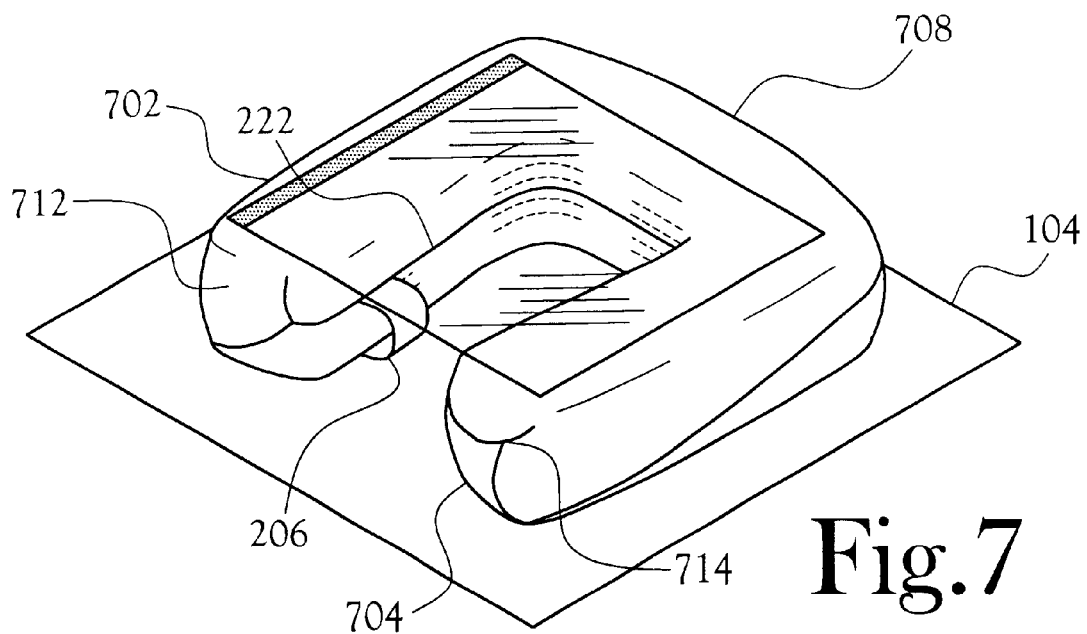
FIG. 7 is a perspective view of the embodiment illustrated in FIG. 6.

FIG. 6 illustrates a tube sheet 602 for another embodiment of the present invention, which is illustrated in FIG. 7. The tube sheet 602, instead of being laid flat during fabrication, has excess material 604, 606 which is folded over along the length of each leg 302, 304. After the tube sheet 602 is attached to its mating tube sheet 504, the tube legs 702, 704 have a greater height than without using the excess material 604, 606. The excess material 604, 606 at the end of the tube legs 702, 704 can be seen in FIG. 7 as a puckered area 712, 714 at the seam 222. As can be seen in FIG. 7, with the upper tube sheet 602 having excess material 604, 606, the seam 222 on the outside of the tube legs 702, 704 is positioned closer to the base sheet 104 at the end of the tube leg 702, 704 opposite the connection to the crosspiece 708. In another embodiment, both the top and bottom tube sheets 502, 504 are similar to the tube sheet 602 with excess material 604, 606. A tube fabricated with excess material 604, 606 on both the top and bottom tube sheet 502, 504 has legs 702, 704 with a greater height, which results in the cover sheet 106 being supported more by the tube legs 702, 704 than the face of the patient 110.

Figure 8:
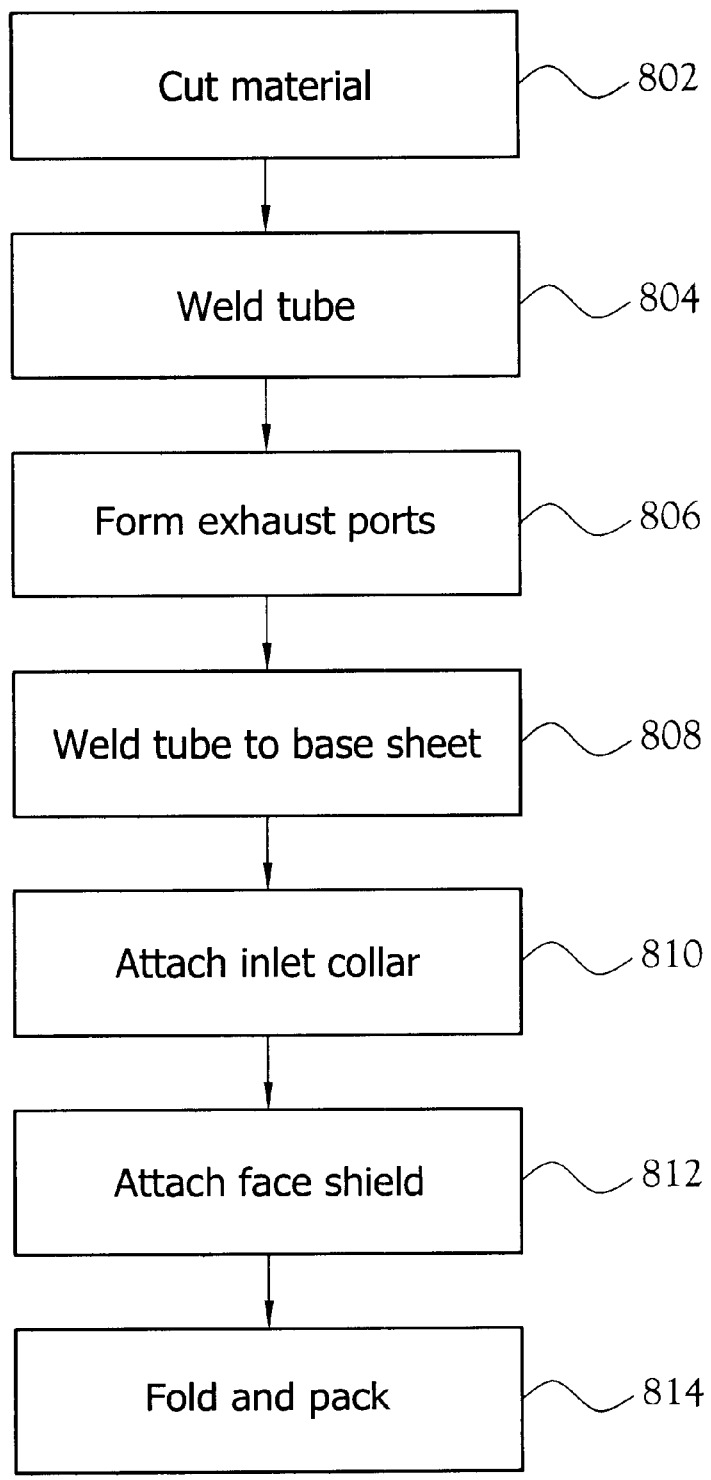
FIG. 8 is a block diagram showing the steps of fabricating one embodiment of the therapy device.

FIG. 8 is a flow diagram showing the steps of fabricating the therapy device 10. The first step is to cut the material 802. Once the material is cut, the tube sheets 502, 504 can be sealed at their common edges 222 by welding 804 or other means for making an air tight seal.

In the illustrated embodiment, the exhaust ports 212 are slits cut parallel to a tangent line of the tube sheet 502, 504 edge 222. Once the two tube sheets 502, 504 are fastened together, the exhaust ports 212 are formed 806 by cutting into the material of the tube 102. The exhaust ports 212 can be cut 806 by lancing slits or punching holes in the tube sheets 502, 504. In another embodiment, the exhaust ports 212 are uncoated areas of an air permeable material that is partially coated with a thin film of plastic or other air impermeable material. For this embodiment, when the tube sheet 502, 504 material is coated before cutting, the exhaust ports 212 can be formed 806 before the material is cut. Those skilled in the art will recognize that the number of exhaust ports 212 can vary based on their size and the available air supply flow without departing from the spirit and scope of the present invention.

After the tube sheets 502, 504 are mated 804, the tube 102 is secured to the base sheet 104 by attaching the crosspiece 308 of the tube 102 to the base sheet 104 and by attaching the securing straps 206, 306 to the base sheet 104. The inlet collar 108 is secured 810 to the tube 102 and the cover sheet 106 is attached 812 to the tube 102. Lastly, the assembled therapy device is folded and packed 814, and otherwise made ready for shipment, storage, and use.

In the illustrated embodiment, the patient 110 is positioned on the base sheet 104 with the head of the patient 110 between the legs 302, 304 of the therapy device 10. Heated air is pumped into the therapy device 10 and is exhausted from the exhaust ports 212, which are of a size and number to maintain a back pressure in the therapy device 10, which serves to keep the tube 102 inflated. The cover sheet 106 is extended from one tube leg 302, over the face of the patient 110, and to the other tube leg 304. The therapy device 10 disclosed is suitable for use with a patient 110 off-pump.

From the forgoing description, it will be recognized by those skilled in the art that a therapy device for providing heated air to the upper body of a patient and a method of making the therapy device have been provided. The therapy device is an inflatable U-shaped tube mounted on a base sheet and having a cover sheet. The patient is placed on the base sheet with the patient's head between the legs of the tube. The cover sheet is placed over the patient's face. A heated air supply tube is connected to the tube and the heated air both inflates the tube and is forced out of the exhaust ports of the tube, thereby providing an environment in which a portion of the patient's body is heated.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

Having thus described the aforementioned invention, we claim:

1. A therapy device for providing air to a patient's upper body, said device comprising:
   a tube having a first leg, a second leg, and a crosspiece, said tube having an orifice for an air supply hose, said tube having a plurality of exhaust ports, said tube having a first tube sheet and a second tube sheet joined at a common outside edge, said first tube sheet having said air permeable portion and an air impermeable portion, said air impermeable portion formed by a coating of an air impermeable material applied to a portion of said first tube sheet, said plurality of exhaust ports defined by an air permeable portion of said tube;
   a base sheet attached to said crosspiece; and
   a cover sheet attached to said first leg and extending to said second leg.

2. A therapy device for providing air to a patient's upper body, said device comprising:
   a tube having a first leg, a second leg, and a crosspiece, wherein said first leg, said second leg, and said crosspiece defining a U-shaped opening, said tube having an orifice for an air supply hose, said tube formed by overlaying a first tube sheet and a second tube sheet and joining said first tube sheet and said second tube sheet at a common outside edge;
   a plurality of exhaust ports formed in said tube, said tube having an air permeable portion and an air impermeable portion, said plurality of exhaust ports defined by said air permeable portion of said tube, wherein said air impermeable portion is formed by a coating of an air impermeable material applied to said tube;
   a base sheet attached to said crosspiece;
   at least one securing tab extending from said common outside edge and attached to said base sheet; and
   a cover sheet attached to said first leg, said cover sheet being transparent and extending to said second leg.

3. A therapy device for providing air to a patient's upper body, said device comprising:
   a tube having a first leg, a second leg, and a crosspiece, said tube having an orifice for an air supply hose, said tube having a plurality of exhaust ports;
   a base sheet attached to said crosspiece, whereby said base sheet holds said tube in a fixed position when inflating and deflating said tube;
   at least one securing tab extending from said first leg and attached to said base sheet; and a cover sheet attached to said first leg and extending to said second leg, said tube positioned between said cover sheet and said base sheet.

4. A therapy device for providing air to a patient's upper body, said device comprising:

a tube having a first leg, a second leg, and a crosspiece, said tube having an orifice for an air supply hose, said tube having a plurality of exhaust ports, said plurality of exhaust ports defined by an air permeable portion of said tube, said tube including a first tube sheet and a second tube sheet, said tube formed by overlaying said first tube sheet and said second tube sheet and joining said first tube sheet and said second tube sheet at a common outside edge, said first tube sheet having said air permeable portion and an air impermeable portion, said air impermeable portion formed by a coating of an air impermeable material applied to a portion of said first tube sheet;

a base sheet attached to said crosspiece, whereby said base sheet holds said tube in a fixed position when inflating and deflating said tube; and a cover sheet attached to said first leg and extending to said second leg, said tube positioned between said cover sheet and said base sheet.

5. A therapy device for providing air to a patient's upper body, said device comprising:

a tube having a first leg, a second leg, and a crosspiece, wherein said first leg, said second leg, and said crosspiece defining a U-shaped opening, said tube having an orifice for an air supply hose, said tube formed by overlaying a first tube sheet and a second tube sheet and joining said first tube sheet and said second tube sheet at a common outside edge, said tube having an air permeable portion and an air impermeable portion, said plurality of exhaust ports defined by said air permeable portion of said tube, wherein said air impermeable portion is formed by a coating of an air impermeable material applied to said tube;

a plurality of exhaust ports formed in said tube;

a base sheet attached to said crosspiece, whereby said base sheet holds said tube in a fixed position when inflating and deflating said tube;

at least one securing tab extending from said common outside edge and attached to said base sheet; and a cover sheet attached to said first leg, said cover sheet being transparent and extending to said second leg, said tube positioned between said cover sheet and said base sheet.

6. A method for fabricating a therapy device for providing heated air to a patient's upper body, said method comprising the steps of:

(a) forming a first tube sheet and a second tube sheet with a complementary shape, said complementary shape being generally U-shaped and having a first leg, a second leg, and a crosspiece;

(b) attaching said first tube sheet to said second tube sheet at an outside common edge such that said first tube sheet and second tube sheet form a tube when inflated;

(c) forming exhaust ports in said first tube sheet and said second tube sheet, said step of forming exhaust ports includes selectively coating said first tube sheet with an air impervious material, wherein said first tube sheet is an air permeable material;

(d) attaching said first tube sheet and said second tube sheet to a base sheet;

(e) attaching a cover sheet to said first tube sheet, said cover sheet being attached by fixing one end of said cover sheet to said first leg, said cover sheet extending to said second leg.

* * * * *